United States Patent
Dainobu et al.

(10) Patent No.: US 10,151,691 B2
(45) Date of Patent: Dec. 11, 2018

(54) GAS SENSOR KIT AND GAS MEASUREMENT SYSTEM

(71) Applicant: NIHON KOHDEN CORPORATION, Tokorozawa (JP)

(72) Inventors: Hidetoshi Dainobu, Tokorozawa (JP); Masayuki Inoue, Tokorozawa (JP); Katsuhide Tone, Tokorozawa (JP); Takanori Sato, Tokorozawa (JP); Kazunori Yoshifuku, Tokorozawa (JP)

(73) Assignee: Nihon Kohden Corporation, Tokorozawa (JP)

( * ) Notice: Subject to any disclaimer, the term of this patent is extended or adjusted under 35 U.S.C. 154(b) by 230 days.

(21) Appl. No.: 15/197,205

(22) Filed: Jun. 29, 2016

(65) Prior Publication Data
US 2016/0377532 A1    Dec. 29, 2016

(30) Foreign Application Priority Data

Jun. 29, 2015    (JP) .................................. 2015-129536

(51) Int. Cl.
| | | |
|---|---|---|
| *G01N 21/35* | (2014.01) | |
| *G01N 33/497* | (2006.01) | |
| *G01N 21/3504* | (2014.01) | |
| *G01L 19/00* | (2006.01) | |

(52) U.S. Cl.
CPC ...... *G01N 21/3504* (2013.01); *G01L 19/0092* (2013.01); *G01N 33/497* (2013.01); *G01N 2201/062* (2013.01)

(58) Field of Classification Search
CPC ............................................... G01N 21/3504
See application file for complete search history.

(56) References Cited

U.S. PATENT DOCUMENTS

| | | | | |
|---|---|---|---|---|
| 5,869,749 A | * | 2/1999 | Bonne .................... | G01N 21/03 250/339.12 |
| 2008/0161711 A1 | * | 7/2008 | Orr ....................... | A61B 5/0833 600/532 |
| 2010/0012417 A1 | * | 1/2010 | Walter ................. | B60K 28/063 180/272 |
| 2016/0149394 A1 | * | 5/2016 | Trusty ................... | H02H 5/083 361/59 |

FOREIGN PATENT DOCUMENTS

| | | |
|---|---|---|
| JP | 02-131410 U1 | 1/1994 |
| JP | 2013136059 A | 7/2013 |

* cited by examiner

*Primary Examiner* — David Porta
*Assistant Examiner* — Jeremy S Valentiner
(74) *Attorney, Agent, or Firm* — Dorsey & Whitney LLP

(57) ABSTRACT

To provide a gas sensor kit and a gas measurement system in which a problem in arrangement of a signal processor and an atmospheric pressure sensor at the time of measuring a gas is solved. A gas sensor kit includes a sensor and a connector. The connector includes an atmospheric pressure sensor measuring an atmospheric pressure and a signal processor. The signal processor receives a measurement signal indicating a transmitted light quantity of a target gas from the sensor and obtains a measurement value of a concentration or a partial pressure of the target gas based on the measurement signal. The signal processor corrects the measurement value of the concentration or the partial pressure of the target gas by using an atmospheric pressure value measured by the atmospheric pressure sensor.

19 Claims, 7 Drawing Sheets

GAS SENSOR KIT AND GAS MEASUREMENT SYSTEM

CROSS REFERENCE TO RELATED APPLICATION(S)

This application claims priority to and the benefit under 35 U.S.C. § 119(a) of the earlier filing date of Japanese Patent Application No. 2015-129536 filed Jun. 29, 2015, the disclosure of which is hereby incorporated by reference, in its entirety, for any purpose.

BACKGROUND

1. Field of the Invention

The present invention relates to a gas sensor kit and a gas measurement system.

2. Description of Related Art

Various apparatuses and methods for monitoring respiration of a patient (person to be measured) requiring respiratory management in medical sites and so on have been proposed. For example, in a method called capnometry, a respiratory condition of the person to be measured is grasped by measuring partial pressure of carbon dioxide contained in expiratory gas of the person to be measured, namely, change with time in carbon dioxide concentration in the expiratory gas (for example, JP-UM-A-2-131410 (Patent Document 1). The system for implementing capnometry is roughly divided into a sidestream type and a mainstream type.

A mainstream type CO2 sensor kit includes a sensor obtaining a signal relating to a concentration (or partial pressure) of carbon dioxide, a cable connecting the sensor to a connector and a connector connecting the cable to a host device (for example, a patient monitor).

SUMMARY OF THE INVENTION

According to an embodiment of the present invention, there is provided a gas sensor kit including a sensor and a connector, in which the sensor irradiates a range to be measured of a target gas with given light and receives transmitted light transmitted through the range to be measured, and the connector has an atmospheric pressure sensor measuring an atmospheric pressure, and a signal processor receiving a measurement signal indicating a transmitted light quantity from the sensor, obtaining a measurement value of a concentration or a partial pressure of the target gas based on the measurement signal, and correcting the measurement value by using an atmospheric pressure value measured by the atmospheric pressure sensor.

Also according to the embodiment of the present invention, there is provided a gas measurement system including a gas sensor kit having a sensor and a connector, and a host device, in which the sensor irradiates a range to be measured of a target gas with given light and receives transmitted light transmitted through the range to be measured, the connector receives a measurement signal indicating a transmitted light quantity from the sensor, obtains a measurement value of a concentration or a partial pressure of the target gas based on the measurement signal, and corrects the measurement value by using an atmospheric pressure value measured inside the connector, and the host device displays the corrected measurement value which is received from the connector.

In the above structure, the signal processor and the atmospheric pressure sensor are mounted inside the connector. Accordingly, it is possible to avoid the sensor apparatus from increasing in size. As the signal processor calculates the corrected measurement value of the concentration or the partial pressure of the target gas, processing relating to the gas measurement in the host device is not required, which can simplify the structure of the host device.

According to the present invention, the gas sensor kit and the gas measurement system capable of avoiding problems of the size increase of the sensor body and the complication of the apparatus which occur due to the arrangement of the signal processor and the atmospheric pressure sensor can be provided.

DETAILED DESCRIPTION

In the measurement using the mainstream type CO2 sensor kit, a signal processor which processes an analog signal obtained by the sensor and converts the signal into the concentration (or partial pressure) of carbon dioxide is necessary. The signal processor is provided, for example, in the following (1) to (3).
 (1) the host device
 (2) the cable connecting the connector to the host device
 (3) a sensor body (a sensor detachable to an airway adapter)

When the signal processor is arranged in the host device (above (1)), the degree of freedom in design of the host device is reduced. When the signal processor is arranged inside the cable (above (2)), it may be an obstacle for a user (a doctor or the like) at the time of operating the system. When the signal processor is arranged in the sensor body (above (3)), the weight of the sensor body is increased, therefore, a load is added to an intubation tube.

It is known that a measurement value by the capnometry varies under the influence of variation in atmospheric pressure. In response, a gas measuring apparatus correcting a measurement value of a target gas by using the measured air pressure is disclosed in JP-A-2013-68456 (Patent Document 2). However, the gas measuring apparatus has a pressure sensor and a correction processor using an atmospheric pressure value inside a host device, therefore, there is a problem that the complexity of the apparatus is increased (in other words, the degree of freedom in design of the host device is reduced).

The problem in arrangement of the signal processor and the atmospheric pressure sensor similarly exists not only in the case where the target gas is a carbon dioxide gas but also in the case of a volatile anesthetic gas, a laughing gas or the like. Accordingly, an object of the present invention is to provide a gas sensor kit and a gas measurement system in which the problem in arrangement of the signal processor and the atmospheric pressure sensor is solved.

<Embodiment 1>

Figure 1:
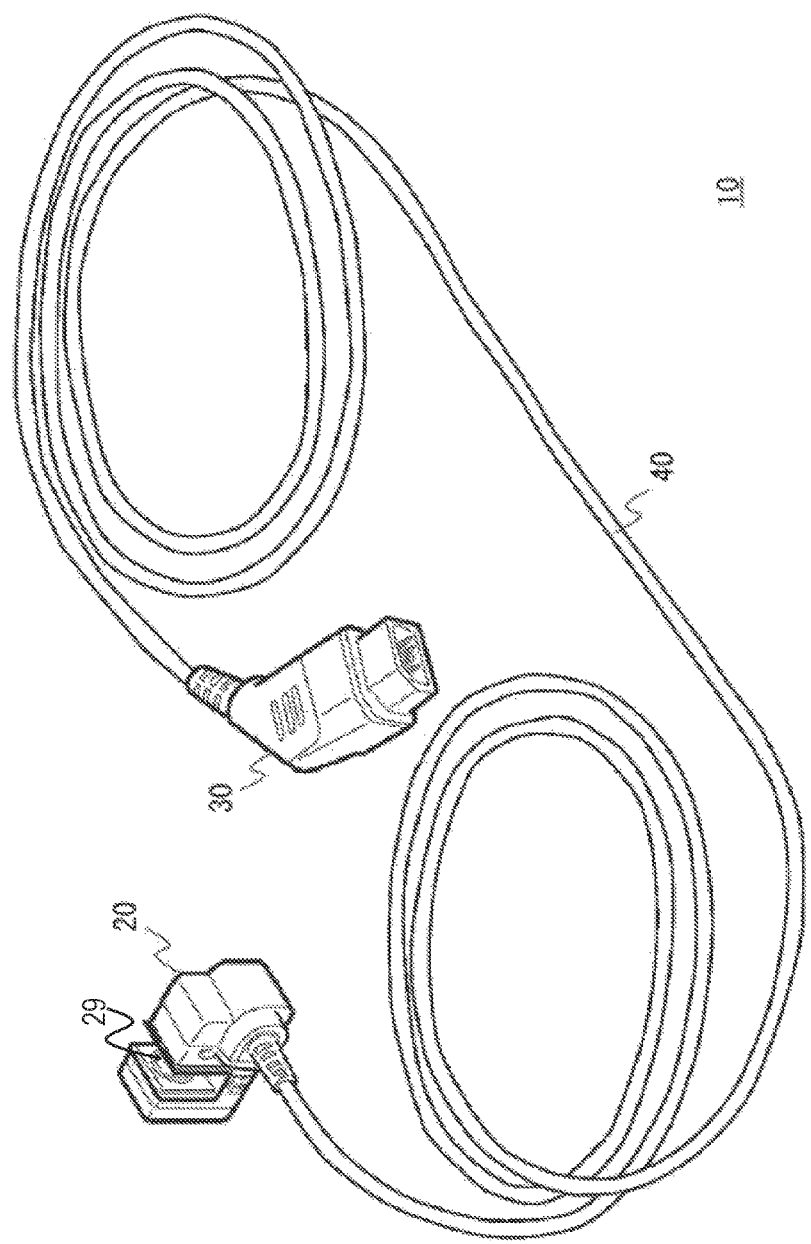
FIG. 1 is a diagram showing an external view of a gas sensor kit according to Embodiment 1.

Hereinafter, an embodiment of the present invention will be explained with reference to the drawings. FIG. 1 is a conceptual diagram showing an external structure of a gas sensor kit 10 according to the embodiment. The gas sensor kit 10 includes a sensor 20, a connector 30 and a cable 40.

The gas sensor kit 10 is a mainstream type sensing unit used for measuring gas mainly in medical sites. The gas sensor kit 10 is used by connecting the connector 30 to a host device 50 (not shown in FIG. 1). Target gases to be measured by the gas sensor kit 10 are, for example, a carbon dioxide gas, an oxide gas, a volatile anesthetic gas and a laughing gas.

The sensor 20 is a sensor capable of detecting given target gases (the carbon dioxide gas, the oxide gas, the anesthetic gas, the laughing gas and so on) included in expiratory gas of a living body. In the following explanation, the target gas to be measured is the carbon dioxide gas.

In an airway adapter, a passage allowing the expiratory gas of a subject to pass through is formed. When the concentration of the carbon dioxide gas contained in the expiratory gas of the subject is measured, an optical axis 29 connecting a light emitting part (a later-described infrared light source 27) and light receiving parts (later-described photodetectors 21 and 24) provided in the sensor 20 is arranged so as to cross the passage (range to be measured). Infrared light emitted from the light emitting part is received by the light receiving parts, and a measurement value corresponding to the light receiving intensity is outputted from the sensor 20 through the connector 30 (detection of carbon dioxide). The carbon dioxide has a property of strongly absorbing infrared light of a particular wavelength, therefore, the higher the concentration of carbon dioxide in the expiratory gas is, the more strongly the infrared light is absorbed, which reduces the transmitted light quantity. Accordingly, the concentration (or partial pressure) of carbon dioxide contained in the expiratory gas of the subject can be measured by monitoring the signal intensity (transmitted light quantity) outputted from the sensor 20.

The cable 40 physically connects the sensor 20 to the connector 30, transmitting an output digital signal from the sensor 20 to the connector 30. That is, the cable 40 is extended from the sensor 20 and transmits the signal to the connector 30.

Figure 2:
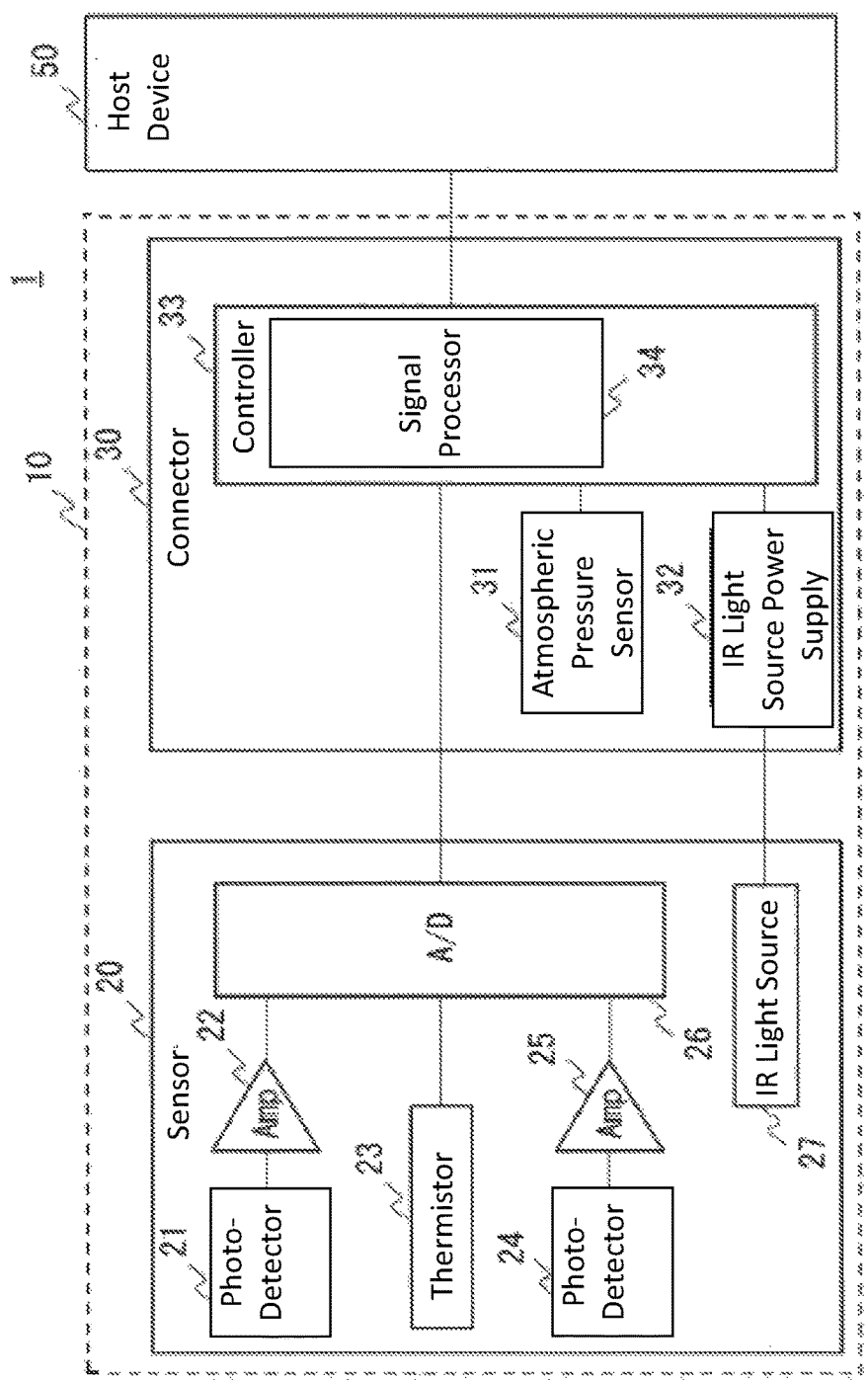
FIG. 2 is a block diagram showing a measurement system according to Embodiment 1.

The connector 30 configures a connecting part for connecting to the later-described host device 50 (FIG. 2). The connector 30 is connected to the host device 50 (FIG. 2), for example, through physical connector pins. The connector 30 includes an atmospheric pressure sensor for measuring atmospheric pressure for correcting the calculated concentration (or partial pressure) of carbon dioxide. Accordingly, the connector 30 includes a communicating part communicating the atmospheric pressure sensor to outer air. The details of the structure will be explained later with reference to FIG. 4 to FIG. 7 and so on.

Subsequently, the summary of a gas measurement system 1 including the gas sensor kit 10 will be explained with reference to FIG. 2. The gas measurement system 1 includes the gas sensor kit 10 and the host device 50. The host device 50 may be a so-called capnometer, a patient monitor and so on having other monitoring functions together with functions of the capnometer or other devices.

The gas sensor kit 10 includes the sensor 20 and the connector 30 as described above. The sensor 20 includes the photodetector 21, an amplifier 22, a thermistor 23, the photodetector 24, an amplifier 25, an A/D (analog/digital) converter 26 and the infrared (IR) light source 27.

The infrared light source 27 is driven by supplying power from an infrared (IR) light source power supply 32. The infrared light source 27 irradiates the airway adapter (not shown) with two kinds of infrared lights having different wavelengths (hereinafter referred to as a first infrared light and a second infrared light). The first infrared light is a light ray for measuring the concentration of the carbon dioxide gas contained in the expiratory gas of the subject and the second infrared light is a light ray for reference which is referred to at the time of measuring gas. The infrared light source 27 is configured by, for example, a LED (Light Emitting Diode), a filament lamp and so on which can emit infrared light.

The photodetector 21 receives transmitted light obtained by the first infrared light being transmitted through the airway adapter. The quantity of the first infrared light to be absorbed varies in accordance with the concentration of the carbon dioxide gas contained in the expiratory gas of the subject, which is reflected on the intensity of infrared light received by the photodetector 21. The photodetector 21 outputs a voltage signal corresponding to the intensity of light received by a light receiving surface (a measurement signal indicating the transmitted light quantity) to the A/D converter 26 through the amplifier 22.

The photodetector 24 receives transmitted light obtained by the second infrared light being transmitted through the airway adapter. The second infrared light is an infrared light having a wavelength not absorbed by carbon dioxide, and the intensity of infrared light received by the photodetector 24 is almost fixed regardless of the concentration of the carbon dioxide gas contained in the expiratory gas of the subject. The photodetector 24 outputs a voltage signal corresponding to the intensity of light received by a light receiving surface (a measurement signal indicating the transmitted light quantity) to the A/D converter 26 through the amplifier 25.

As the sensitivities of the photodetector 21 and the photodetector 24 for infrared light generally vary according to the temperature, the sensitivities of the photodetector 21 and the photodetector 24 are temperature-corrected by using the thermistor 23. It is also preferable to control peripheral temperatures of the photodetector 21 and the photodetector 24 to be constant by further providing a heater and so on.

The A/D converter 26 converts the measurement signal (voltage signal indicating the transmitted light quantity) detected by the photodetector 21 and the measurement signal (voltage signal indicating the transmitted light quantity) detected by the photodetector 24 into measurement signals in a digital format. The A/D converter 26 transmits the measurement signals after the conversion to the connector 30 through the cable 40 (FIG. 1).

The connector 30 includes an atmospheric pressure sensor 31, the infrared light source power supply 32, a controller 33 and a signal processor 34. The connector 30 also includes various memory devices, calculation circuits and so on, although not shown.

The atmospheric pressure sensor 31 is a sensor which measures an ambient pressure by providing, for example, a pressure-sensitive device thereinside. The atmospheric pressure sensor 31 outputs an atmospheric pressure value obtained to the signal processor 34. The infrared light source power supply 32 supplies power to the infrared light source 27 inside the sensor 20.

The controller 33 performs control of respective processors inside the connector 30, which includes various circuits and a CPU (Central Processing Unit) executing programs. The signal processor 34 configures part of the controller 33, calculating the concentration (or partial pressure) of the carbon dioxide gas contained in the expiratory gas of the subject.

The measurement signals detected by the photodetector 21 and the photodetector 24 are inputted to the signal processor 34 as digital values as described above. The signal processor 34 calculates the concentration (or partial pressure) of the carbon dioxide gas based on a ratio of these two measurement signals. For example, the signal processor 34 reads out a table which is previously defined from a memory device (not shown). The table defines the relation between the ratio of measurement signals detected by the photodetector 21 and the photodetector 24 and the concentration (or partial pressure) of the carbon dioxide gas contained in the expiratory gas of the subject. The signal processor 34 calculates the measurement value of the concentration (or partial pressure) of the carbon dioxide gas contained in the expiratory gas of the subject by comparing an actual value of the measurement signal and the table.

The signal processor 34 may calculate the concentration (or partial pressure) of the carbon dioxide gas by using the relation (an attenuation rate of light) between the light receiving quantity (transmitted light quantity) of the photodetector 21 and the light receiving quantity (transmitted light quantity) of the photodetector 24, not limited to the processing using the table. It is theoretically possible that the signal processor 34 calculates the concentration (or partial pressure) of the carbon dioxide gas by performing measurement by using light of one wavelength only inside the sensor 20 (namely, a structure in which the photodetector 24 and the amplifier 25 do not exist) and by using the light emitting quantity and the light receiving quantity (transmitted light quantity) of the photodetector 21 only.

That is, the calculation processing of the concentration (or partial pressure) of the carbon dioxide gas by the signal processor 34 may be common processing used in the mainstream type capnometry, and any type of processing may be adopted as long as the transmitted light quantity of the target gas is used.

Furthermore, the atmospheric pressure value measured by the atmospheric pressure sensor 31 is inputted to the signal processor 34. The signal processor 34 corrects the calculated measurement value of the concentration (or partial pressure) of the carbon dioxide gas by using the atmospheric pressure. Various methods of correcting the measurement value of the concentration or the partial pressure by the air pressure can be considered according to the target gas and the measuring method (the principle and structure), therefore, a method which has been hitherto adopted may be used, and detailed explanation is omitted.

The structure of the gas measurement system 1 according to the embodiment focusing on electrical processing has been explained as the above. Here, advantages obtained by the above structure will be explained. When the measurement value of the concentration or the partial pressure of the target gas (for example, the concentration or the partial pressure of the carbon dioxide gas) is calculated, the correction is required to be performed by using the atmospheric pressure value. Here, it is not preferable that the atmospheric pressure sensor 31 is set inside the sensor 20 as the structure of the sensor 20 is increased in size. In particular, the sensor 20 may be used for an infant, therefore, it is desirable to have the minimum internal structure. If the processors relating to the measurement of the target gas and the atmospheric pressure sensor 31 are mounted on the host device 50, the degree of freedom in design inside the host device 50 is drastically reduced. In particular, when the host device 50 is the patient monitor measuring many parameters, the complexity of the apparatus is drastically increased as the sensors and the like used only for measuring the target gas are mounted inside the patient monitor.

On the other hand, in a structure shown in FIG. 2, the signal processor 34 and the atmospheric pressure sensor 31 are mounted inside the connector 30. Accordingly, it is possible to prevent the sensor 20 from increasing in size. The signal processor 34 also calculates the measurement value of the concentration or the partial pressure of the target gas and transmits the value to the host device 50. In other words, the host device 50 can directly use the received measurement value of the concentration or the partial pressure of the target gas (for example, host device 50 can display the value on a display or can control the ringing of an alarm using the measurement value). For example, the host device 50 displays a respiration waveform and the like on the display by using the received measurement value of the concentration or the partial pressure of the target gas. Accordingly, the complication of the structure of the host device 50 can be avoided. Furthermore, the host device 50 can use (display and so on) the accurate measurement value which has been corrected even when the host device 50 is an old-type device not having a correction processing ability using the atmospheric pressure.

Subsequently, a casing structure of the connector 30 will be explained. The casing of the connector 30 has a shape of a male connector to be inserted into a female connector of the host device 50 as shown in FIG. 1. The connector 30 may be other types of connectors, not limited to the male connector.

Figure 3:
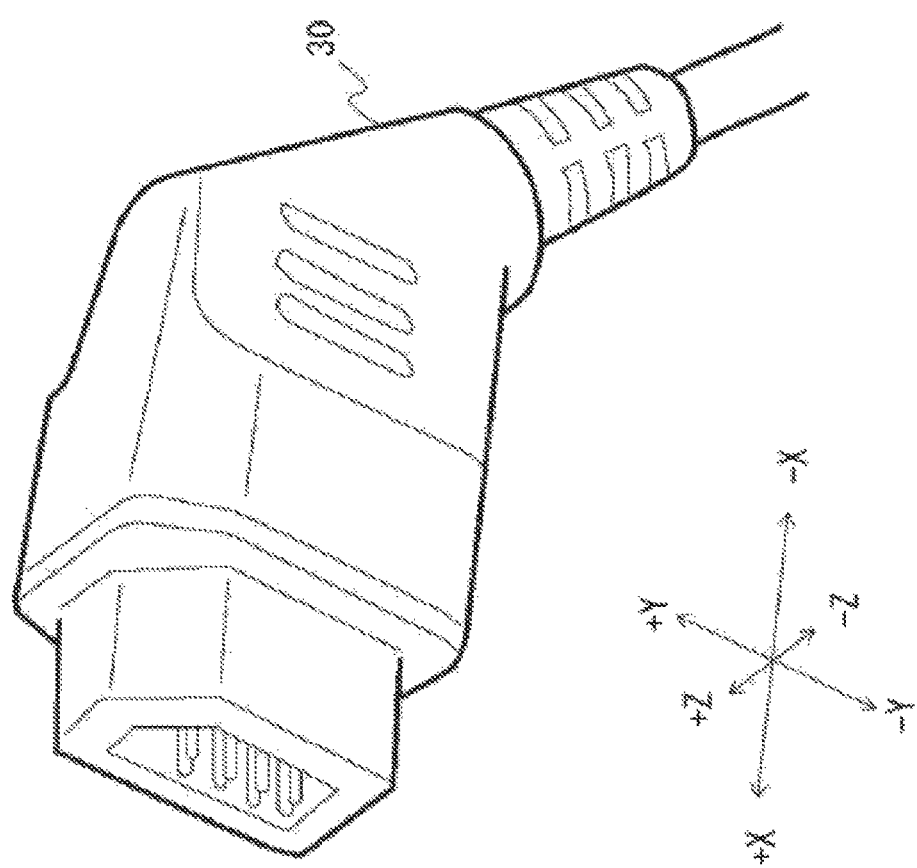
FIG. 3 is a diagram showing an external structure of a connector according to Embodiment 1.

FIG. 3 is an enlarged diagram of the connector 30 according to the embodiment. As shown in FIG. 3, a direction of inserting connector pins is regarded as +X direction and a reverse direction is regarded as −X direction. +Y direction, −Y direction, +Z direction and −Z direction are directions respectively shown in FIG. 3. That is, a long axis direction of an insertion port with respect to the host device 50 (a surface on which the connector pins are mounted) is set to Y direction and a short axis direction is set to Z direction.

Figure 4:
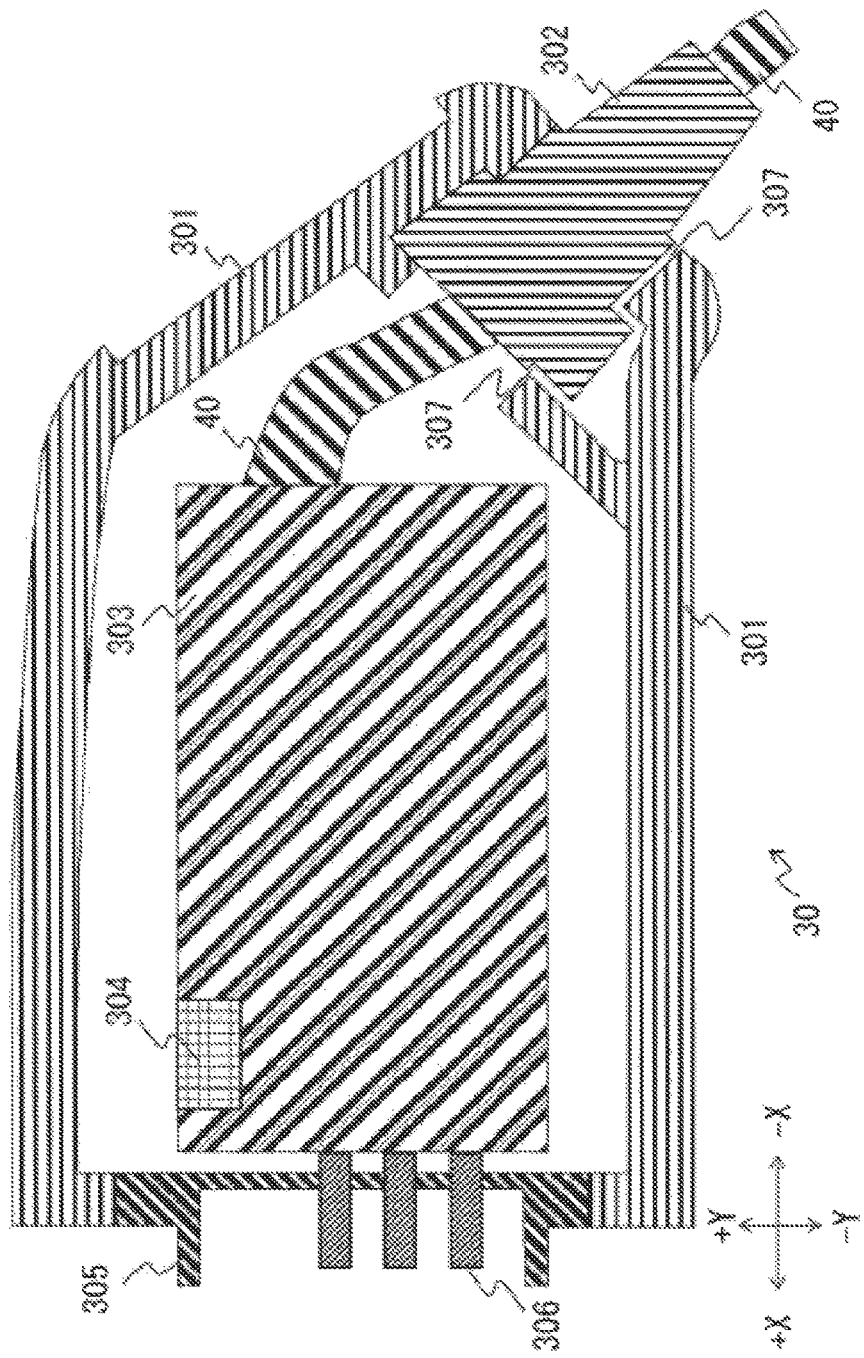
FIG. 4 is a cross-sectional view of the connector according to Embodiment 1.

FIG. 4 is an X-Y cross-sectional view of the connector 30. The cross-sectional view of FIG. 4 is shown by simplifying part of the structure including the number of connector pins and so on for easier comprehension. The casing of the connector 30 includes exterior casing members 301 and a connecting surface casing member 305. A structure in which the exterior casing members 301 and the connecting surface casing member 305 are united may be adopted.

A fixing member 302 is a member for fixing the cable 40 to the connector 30. In the example, the fixing member 302 is locked to convex-concave portions of the exterior casing members 301, thereby fixing the cable 40 to the connector 30.

In the casing of the connector 30, a communicating part for securing inflow of outside air into the connector 30 is provided. The communicating part in the example in FIG. 4 is formed by a groove 307 provided on the fixing member 302. The groove 307 forms a gap between the inside of the connector 30 and the cable 40. An external structure of the fixing member 302 having the groove 307 will be explained with reference to FIG. 5.

Figure 5:
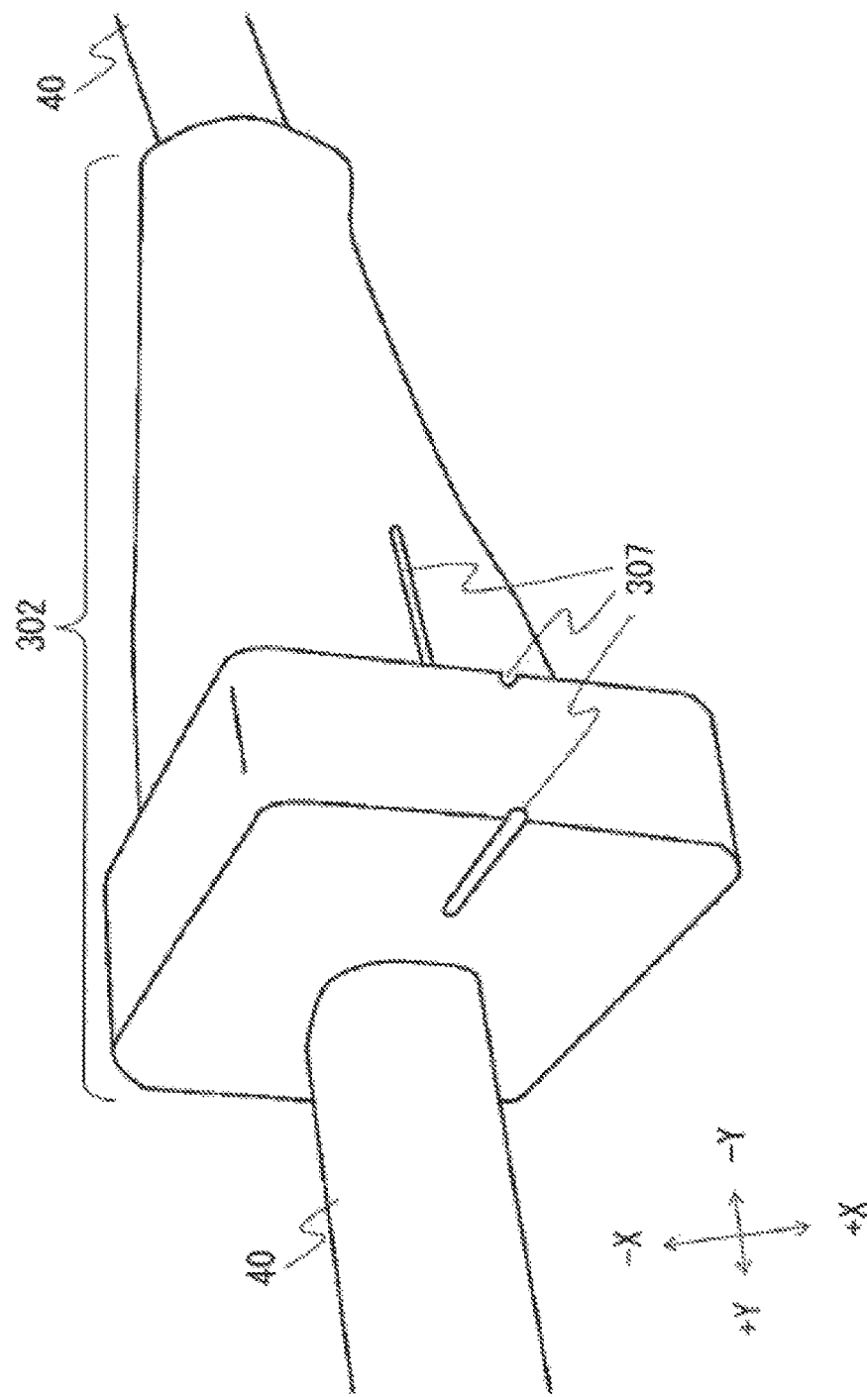
FIG. 5 is a perspective view of a fixing member according to Embodiment 1.

FIG. 5 is a perspective view displayed by enlarging parts of the fixing member 302 and the cable 40. As shown in the drawing, the groove 307 having a width and a depth which can be a flow path of outside air while keeping a waterproof property is formed on the surface of the fixing member 302. The groove 307 have approximately 0.3 mm to 0.7 mm in width and depth. As the groove 307 is formed, it is possible to take outside air into the connector 30. As the size is sufficiently small, the waterproof property can be kept. The above size of the groove 307 (approximately 0.3 mm to 0.7 mm in width and depth) is just an example, and other sizes may be adopted as long as the waterproof property is kept while taking in outside air.

Refer to FIG. 4 again. A printed circuit board 303 is disposed inside the connector 30. The printed circuit board 303 is provided with an atmospheric pressure sensor 304 (corresponding to the atmospheric sensor 31 in FIG. 2). On the printed circuit board 303, circuits, a CPU, memory devices and so on for realizing various functions of the controller 33 are mounted. The printed circuit board 303 transmits signals to the connected host device 50 through connector pins 306.

As described above, the groove 307 becomes the inflow path of outside air to the inside of the connector 30. Accordingly, the atmospheric pressure sensor 304 can measure the air pressure of outside air flowing through the groove 307. A place where the groove 307 is provided is not limited to the place shown in FIG. 4 and FIG. 5. That is, the place where the groove 307 is provided is not particularly limited as long as they are places whereby a gap is formed between the cable 40 and the inside of the connector 30. It is also theoretically possible to adopt a structure in which the fixing member 302 does not exist in the connector 30 and a groove corresponding to the groove 307 is provided in the cable 40 itself. That is, the groove corresponding to the groove 307 is provided in a place where the cable 40 contacts the connector 30, and outside air is taken in from the place where the groove corresponding to the groove 307 is provided (a gap in the cable 40) into the connector 30. Also according to the structure, it is possible to take in outside air into the connector 30 and to measure an accurate atmospheric pressure. It is also preferable to provide the groove corresponding to the groove 307, for example, at a place where the exterior casing member 301 contacts the connecting surface casing member 305, not limited to the place between the cable 40 and the connector 30.

The structure of the connector 30 shown in FIG. 4 and FIG. 5 is just an example of the structure having the communicating part for securing the inflow path of outside air into the connector 30, and there are various modification examples in which the communicating part is formed. Hereinafter, modification examples will be explained.

Figure 6:
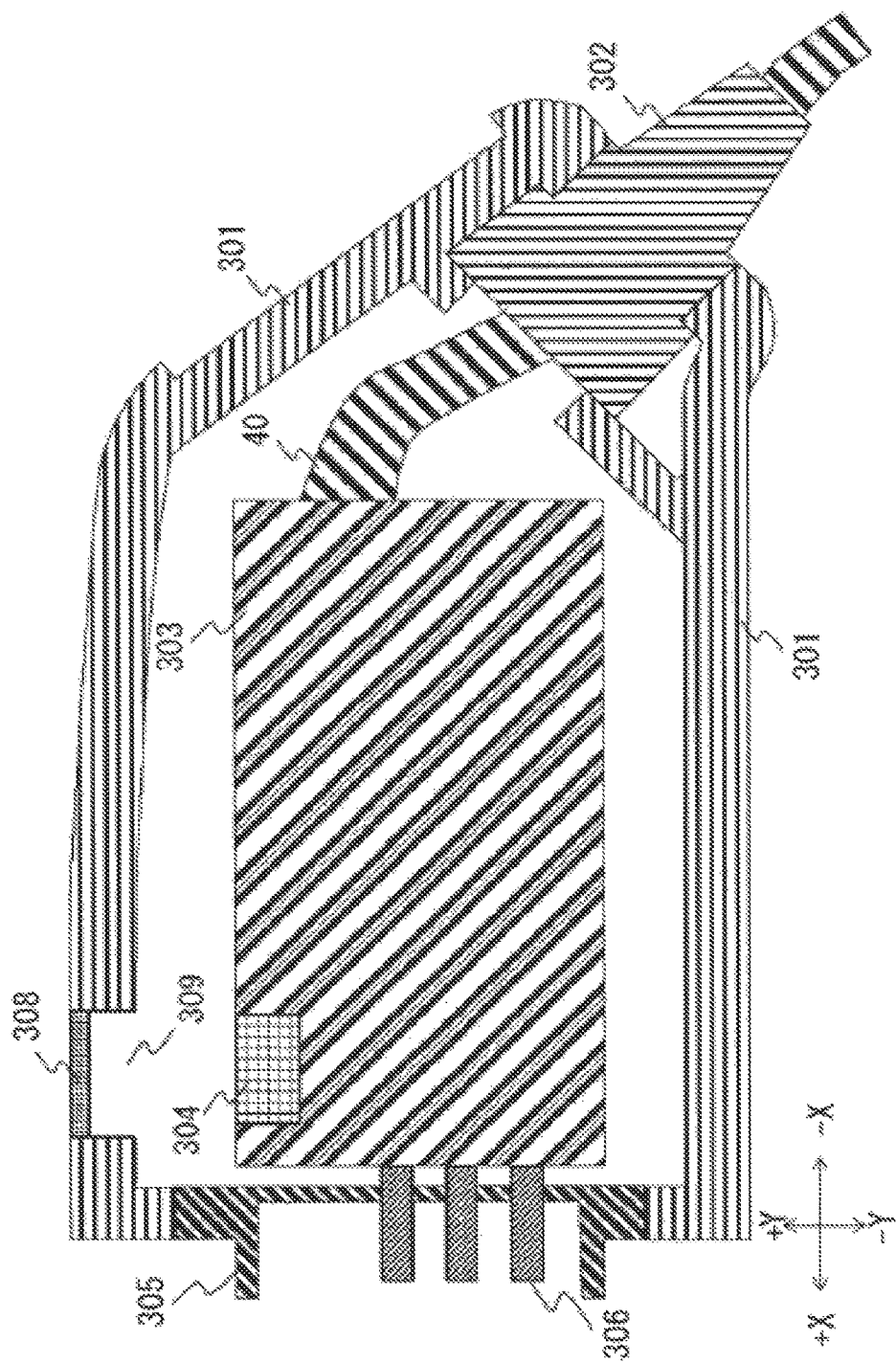
FIG. 6 is a cross-sectional view of the connector according to Embodiment 1.

FIG. 6 is a cross-sectional view showing a first modification example of the connector 30. In the example, the groove 307 is not provided between the fixing member 302 and the exterior casing member 301. In other words, the fixing member 302 is fitted to the exterior casing members 301, and a portion between the fixing member 302 and the exterior casing members 301 is sealed.

In the modification example, a communicating part for securing the flow path of outside air into the connector 30 is configured by a breathable waterproof sheet 308 and a through hole 309. The through hole 309 is, for example, a hole provided on the exterior casing member 301 and may have a size which can be the inflow path of outside air. The breathable waterproof sheet 308 is a material for realizing waterproof while securing breathability. The breathable waterproof sheet 308 may be a sheet material formed by, for example, stacking extra-fine long fibers of polyethylene at random and connecting the fibers. The breathable waterproof sheet 308 is arranged at a place so as to completely cover the through hole 309. In the structure, the inflow path of outside air into the connector 30 is secured by the breathable waterproof sheet 308 and the through hole 309. That is, the atmospheric pressure sensor 304 measures the pressure of outside air flowing through the breathable waterproof sheet 308 and the through hole 309.

The structure shown in FIG. 6 is just an example, and the place where the through hole 309 is provided may be on the exterior casing member 301 side in −Y direction.

Figure 7:
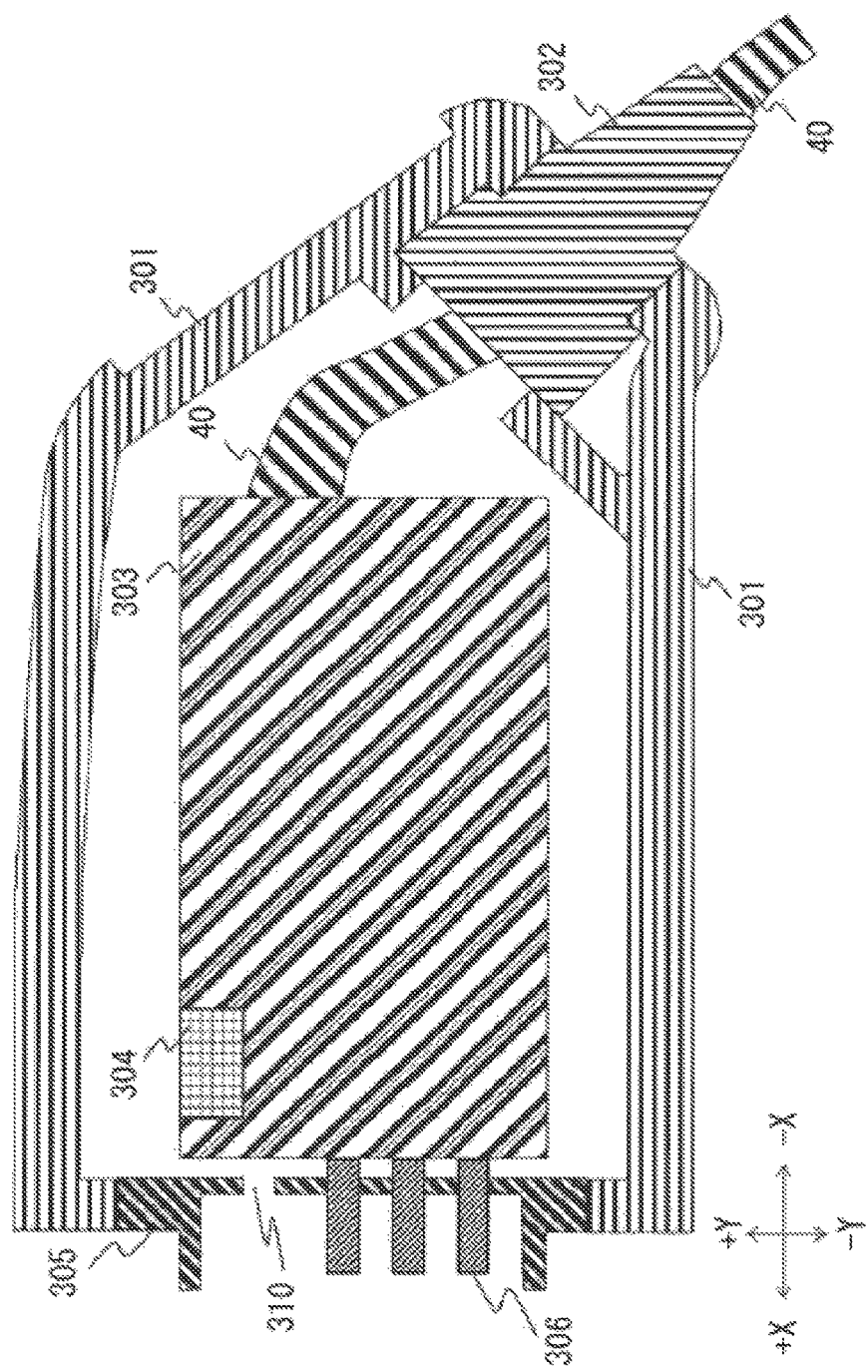
FIG. 7 is a cross-sectional view of the connector according to Embodiment 1.

Subsequently, a second modification example of the connector 30 will be explained with reference to FIG. 7. FIG. 7 is a cross-sectional view showing a second modification example of the connector 30. In the example, the groove 307 is not provided between the fixing member 302 and the exterior casing member 301 in the same manner as FIG. 6.

In the example, a through hole 310 is provided in the connecting surface casing member 305 in addition to the connector pins 306. That is, the through hole 310 is provided on a mounting surface where the connector pins 306 are mounted. The through hole 310 may have a size equivalent to a hole for inserting the connector pin 306. The through hole 310 can be the flow path for taking in outside air from the casing of the host device 50 side when the connector 30 is connected to the host device 50. Accordingly, the atmospheric pressure sensor 304 measures the pressure of outside air flowing through the through hole 310.

Other modification examples may be adopted though not shown. For example, the connector 30 is configured by bonding two exterior casing members 301 by a so-called adhesive. At this time, the adhesive is not applied only to one place (or the usage of the adhesive is reduced as compared with other places). That is, one place of the casing is not sealed and other places are sealed. Accordingly, the place will be the communicating part for taking in outside air into the connector 30.

Subsequently, advantages of the gas sensor kit 10 according to the embodiment will be explained. As described above, the connector 30 has the atmospheric pressure sensor 31 and the signal processor 34 thereinside. Accordingly, the gas sensor kit 10 can calculate the measurement value of the concentration or the partial pressure of the target gas which has been corrected (for example, the concentration or the partial pressure of carbon dioxide) while avoiding the sensor 20 from increasing in size. The signal processor 34 transmits the measurement value of the concentration or the partial pressure of the target gas to the host device 50. In other words, the host device 50 can directly use (for example, to display on the display, to ring the alarm using the measurement value) the received measurement value of the concentration or the partial pressure of the target gas (for example, the concentration or the partial pressure of carbon dioxide) without calculation and so on.

As the connector 30 has the atmospheric pressure sensor 31 (atmospheric pressure sensor 304) thereinside as described above, the communicating part (FIG. 4 to FIG. 7) for taking in outside air into the connector 30 is provided. Accordingly, the connector 30 can accurately acquire the atmospheric pressure and can accurately correct the measurement value of the target gas.

As the atmospheric pressure sensor 31 is provided inside the casing of the connector 30, a free space inside the connector 30 can be effectively used as well as the sensor 20 and the host device 50 can be reduced in size and simplified. Furthermore, the communicating part for taking in outside air with respect to the atmospheric pressure sensor 31 is provided in the casing of the connector 30, therefore, the atmospheric pressure sensor 31 can accurately acquire the atmospheric pressure value. In other words, the connector 30 is not sealed, therefore, the accurate atmospheric pressure value can be acquired.

In the case where the communicating part is formed by the groove 307 as shown in FIG. 4 and FIG. 5, the measurement value can be accurately corrected only by providing the groove 307 without changing common components.

In the case where the communicating part is formed by the breathable waterproof sheet 308 and the through hole 309 as shown in FIG. 6, ventilation to the inside of the connector 30 is secured while realizing high waterproof property.

The structure in which the through hole 310 is provided on the mounting surface of the connector pins 306 as shown in FIG. 7 can be realized only by providing an additional through hole for the connector pin 306 in a manufacturing process. That is, it is possible to secure ventilation to the inside of the connector 30 while suppressing the increase in manufacturing costs of the connector 30.

The invention made by present inventors has been specifically explained based on the embodiment as the above, and the present invention is not limited to the above embodiment and various alterations may occur within a scope not departing from the gist thereof.

What is claimed is:

1. A gas sensor kit comprising:
a sensor; and
a connector,
wherein the sensor is configured to irradiate an optical axis in the sensor with given light to measure a target gas along at least a portion of the optical axis, and further configured to receive the given light transmitted through the optical axis of the sensor, and
wherein the connector includes:
an atmospheric pressure sensor mounted within the connector and configured to measure an ambient atmospheric pressure outside the connector, and
a signal processor mounted within the connector and configured to receive a measurement signal indicating a quantity of the given light from the sensor, to obtain a measurement value related to the target gas based on the measurement signal, and further configured to correct the measurement value by using an ambient atmospheric pressure value measured by the atmospheric pressure sensor.

2. The gas sensor kit according to claim 1,
wherein the connector further includes a casing and a communicating part configured to communicate air outside the casing through the communicating part to the atmospheric pressure sensor to measure the ambient atmospheric pressure outside the connector.

3. The gas sensor kit according to claim 2,
wherein the communicating part is a groove provided on a fixing member, the fixing member configured to couple a cable extending from the sensor to the connector.

4. The gas sensor kit according to claim 3,
wherein the groove has a size of 0.3 mm to 0.7 mm in width and depth.

5. The gas sensor kit according to claim 2,
wherein the communicating part is formed so as to cover a through hole provided on the casing with a breathable waterproof sheet.

6. The gas sensor kit according to claim 2,
wherein the communicating part is a through hole provided on a mounting surface of connector pins.

7. The gas sensor kit according to claim 2,
wherein the communicating part is formed by allowing one place in the casing to be unsealed.

8. The gas sensor kit according to claim 2, further comprising:
a cable connecting the connector to the sensor,
wherein the communicating part includes a groove on the cable, the groove configured to communicate the air outside the casing through the groove to the atmospheric pressure sensor to measure the ambient atmospheric pressure outside the connector.

9. The gas sensor kit according to claim 3, wherein the casing includes one or more exterior casing members,
wherein the fixing member is configured to be coupled to a portion of the one or more exterior casing members of the connector.

10. The gas sensor kit according to claim 1, wherein the measurement value related to the target gas is the measurement value of a concentration of the target gas.

11. The gas sensor kit according to claim 1, wherein the measurement value related to the target gas is the measurement value of a partial pressure of the target gas.

12. A gas measurement system comprising:
a gas sensor kit including:
a sensor; and
a connector coupled to the sensor; and
a host device coupled to the connector and configured to monitor functions related to additional devices and a patient,
wherein the sensor is configured to provide a measurement signal based on a target gas,
wherein the connector comprises:
an atmospheric pressure sensor mounted within the connector and configured to measure an ambient atmospheric pressure outside the connector, and
a signal processor mounted within the connector and configured to receive the measurement signal, provide a measurement value based on the measurement signal, and correct the measurement value by using an ambient atmospheric pressure value measured by the atmospheric pressure sensor, and
wherein the host device is configured to display the measurement value from the connector.

13. The gas measurement system of claim 12,
wherein the sensor is configured to irradiate an optical axis in the sensor with given light to measure the target gas along at least a portion of the optical axis, and further configured to receive the given light transmitted through the optical axis of the sensor,
wherein the measurement signal is indicative of a quantity of the given light from the sensor, and
wherein the measurement value is related to a concentration or a partial pressure of the target gas.

14. The gas measurement system of claim 12, wherein the connector further includes a communicating part configured to communicate air outside the connector through the communicating part to the atmospheric pressure sensor to measure the ambient atmospheric pressure outside the connector.

15. The gas measurement system of claim 14, wherein:
the connector further comprises a casing including one or more exterior casing members;
the gas measurement system further comprises a cable extending from the sensor to the connector; and
the connector further comprises a fixing member configured to fix the cable to the connector and further configured to be coupled to a portion of the one or more exterior casing members of the connector.

16. The gas measurement system of claim 15, wherein the communicating part comprises a groove provided on the fixing member.

17. A gas sensor kit comprising:
  a sensor; and
  a connector configured to calculate a measurement value of a concentration or a partial pressure of a target gas along at least a portion of an optical axis of the sensor based on a transmitted light quantity along the optical axis of the sensor,
  wherein the connector comprises:
    a casing,
    an atmospheric pressure sensor positioned within the casing and configured to measure an ambient atmospheric pressure value for correcting the measured value of the target gas,
    a signal processor positioned within the casing and configured to correct the measurement value using the ambient atmospheric pressure value, and
    a communicating part configured to communicate air outside the casing through the communicating part to the atmospheric pressure sensor to measure the ambient atmospheric pressure outside the connector.

18. The gas sensor kit of claim 17, wherein:
  the casing includes one or more exterior casing members;
  the gas sensor kit further comprises a cable extending from the sensor to the connector; and
  the connector further comprises a fixing member configured to fix the cable to the connector and further configured to be coupled to a portion of the one or more exterior casing members of the connector.

19. The gas sensor kit of claim 17, wherein:
  the casing includes one or more exterior casing members; and the communicating part comprises:
    a through hole in at least one of the one or more exterior casing members; and
    a breathable waterproof sheet configured to cover the through hole.

* * * * *